United States Patent [19]

Masaki

[11] Patent Number: 4,786,278

[45] Date of Patent: Nov. 22, 1988

[54] THERAPEUTIC DEVICE FOR IONTOPHORESING CATION AND ANION

[75] Inventor: Kazumi Masaki, Osaka, Japan

[73] Assignee: Ken Hayashibara, Okayama, Japan

[21] Appl. No.: 940,046

[22] Filed: Dec. 10, 1986

[30] Foreign Application Priority Data

Dec. 14, 1985 [JP] Japan ................. 60-281514

[51] Int. Cl.⁴ ............................... A61N 1/30
[52] U.S. Cl. .................... 604/20; 128/803;
200/12; 335/81
[58] Field of Search ............... 604/20; 128/790, 803,
128/800, 801; 335/81; 200/12

[56] References Cited

U.S. PATENT DOCUMENTS 3,163,166 12/1964 Brant et al. ...................... 604/20
4,406,658 9/1983 Lattin et al. ...................... 604/20

FOREIGN PATENT DOCUMENTS 3127231 1/1983 Fed. Rep. of Germany .
2539622 7/1984 France .
113769 4/1945 Sweden ............................ 335/81
2132892 7/1984 United Kingdom ............... 604/20

Primary Examiner—Lee S. Cohen
Attorney, Agent, or Firm—Browdy and Neimark

[57] ABSTRACT

Disclosed is a novel therapeutic device comprising means for generating a low-frequency current in which an undirectional current is superposed on a dc current; means for switching at time intervals the output polarity of said oscillating means; an electrode means which contains an ionized medicament and acts as the active electrode; and another electrode means which acts as the dispersive electrode. A high efficacy that is hardly attainable by iontophoresing either cation or anion is possible by allowing the whole of an ionized medicament such as aminovinyl photosensitizing dye or kojic acid to penetrate into the deeper part of the skin with the device of the invention.

3 Claims, 5 Drawing Sheets $C_{15}H_{17}BrIN_3 : 446.14$

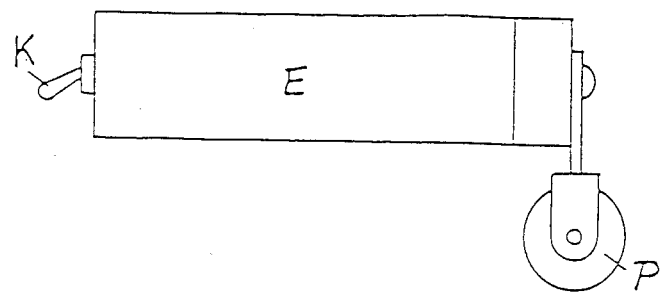
FIG. 8
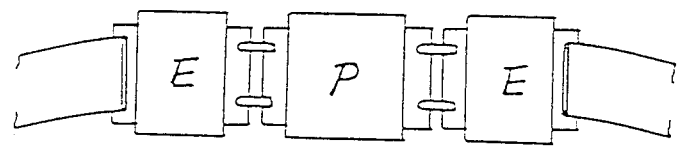
FIG. 9
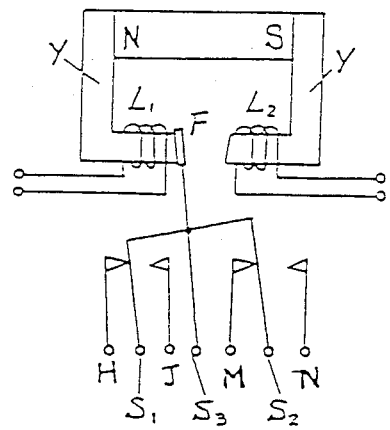

4,786,278

THERAPEUTIC DEVICE FOR IONTOPHORESING CATION AND ANION

BACKGROUND OF THE INVENTION

1. Field of the Invention

The present invention relates to a therapeutic device for iontophoresing both cations and anions of a medicament.

2. Description of the Prior Art

Endermic administration of certain medicaments such as aminovinyl photosensitizing dyes and kojic acid hardly yields a satisfactory efficacy because the medicaments are generally low in skin-permeability.

On investigation of various means for efficiently penetrating the medicaments into the skin, I discovered that the efficacy of the medicaments can be improved by iontophoresis, and disclosed it in Japanese Patent Laid-Open Nos. 221,957/83 and 160,900/85.

Also it was found that the efficacy of certain medicaments still cannot be so improved by iontophoresis. I investigated the cause. As the result, I found that because in conventional devices a low-frequency current of one polarity is energized to the active electrode soaked with an ionized medicament, the whole of the medicament scarcely penetrates into the deeper part of the affected site.

SUMMARY OF THE INVENTION

In view of the foregoing, the main object of the present invention is to provide means for efficiently iontophoresing the whole of an ionized medicament.

This and other objects as may become apparent hereinafter have been attained by the device comprising: means for oscillating a low-frequency current in which an undirctional (i.e., Ac) current is superposed on a dc current; means for switching at time intervals the output polarity of said oscillating means; an electrode means which contains an ionized medicament and acts as the active electrode; and another electrode which acts as the dispersive electrode.

BRIEF DESCRIPTION OF THE DRAWINGS

The present invention will hereinafter be explained with reference to the accompanying drawings in which:

FIG. 7 is a side elevation view of an embodiment according to the invention;

FIG. 8 is a front elevation view of the embodiment;

FIG. 9 shows an automatically-operable polarity switch circuit; and

Figure 4:
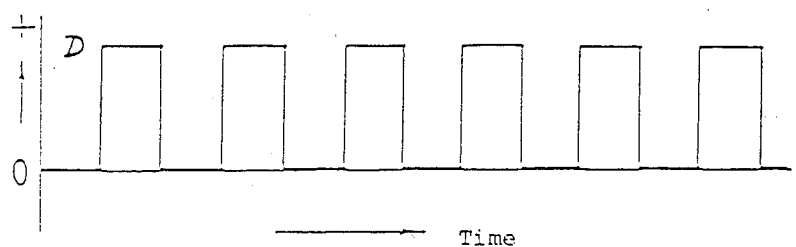
FIG. 4 is the waveform of a positive superposed voltage which is used in iontophoresis according to the invention.

In all the accompanying drawings, symbol G designated a low-frequency biased waveform generator, such as for producing the waveform of FIG. 4, A designates a low-frequency oscillator; B, battery; C, capacitor; E, dispersive electrode; F, movable iron piece; K, power switch; L, coil; P, active electrode; R, resistor; S, polarity switch; SCR, thyristor; and Y, yoke.

DESCRIPTION OF PREFERRED EMBODIMENTS

Figure 1:
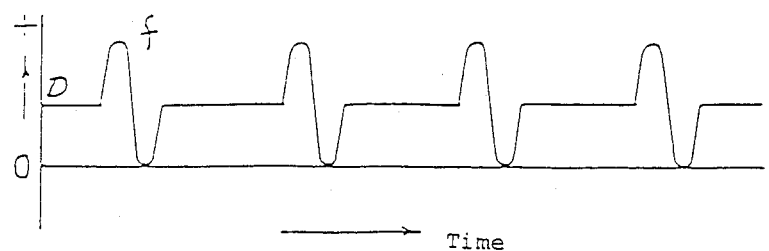
FIG. 1 is the waveform of a current for iontophoresing a cation.

FIG. 1 illustrates a current for iontophoresing a cation, wherein an undirectional (Ac) voltage f is superposed on positive dc voltage D.

Figure 2:
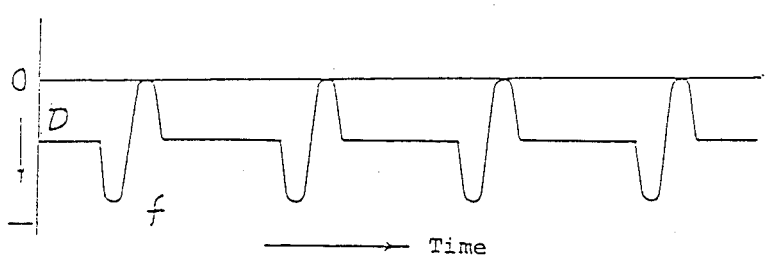
FIG. 2 is the waveform of a current for iontophoresing an anion.

FIG. 2 illustrates a current for iontophoresing an anion, wherein undirectional voltage f is superposed on negative dc voltage D.

Figure 3:
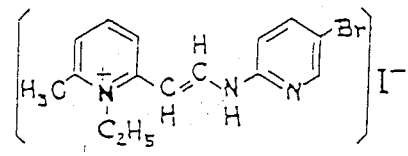
FIG. 3 is the molecular formula of an aminovinyl photosensitizing dye.

The cation and iodide of the aminovinyl photosensitizing dye having the molecular formula as shown in FIG. 3 can be iontophoresed respectively by the positive and negative superposed voltages. Successive application of these superposed voltages penetrates the whole molecule into the deeper part of the skin.

Figure 5:
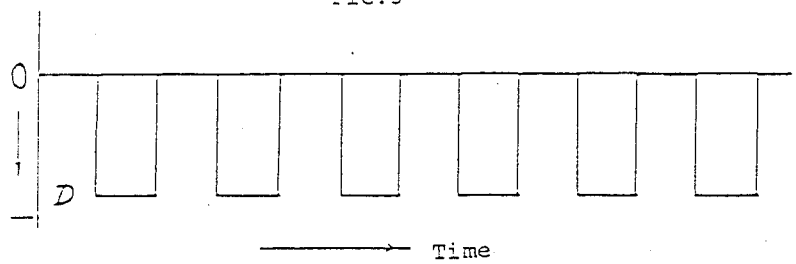
FIG. 5 is the waveform of a negative superposed voltage which is used in iontophoresis according to the invention.

FIGS. 4 and 5 illustrate the waveform of a current for iontophoresis according to the invention, wherein dc voltage D is continually conducted. The positive voltage having the waveform as shown in FIG. 4 is used for iontophoresis of a cation, whereas the negative voltage having the waveform as shown in FIG. 5 is for iontophoresis of an anion.

Figure 6:
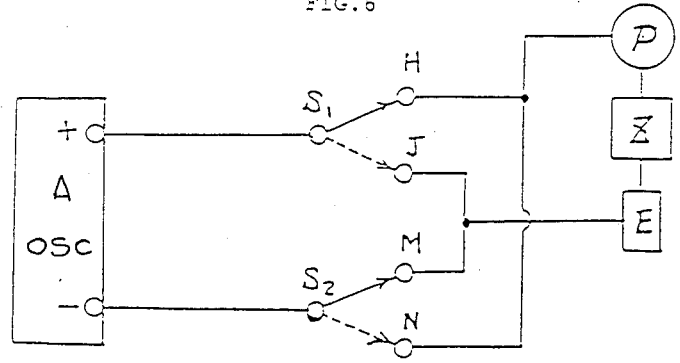
FIG. 6 shows a manually-operable polarity switch circuit.

FIG. 6 illustrates a manually-operable polarity switch circuit. When switches $S_1$ and $S_2$ are in conduction respectively with contacts H and M, a current flows from the positive output of low-frequency oscillator G (biased waveform generator such as for the biased waveform of FIG. 4) (which shows one range of the envelope of the waveform is at ground) to its negative output successively through contact H, active electrode P, load Z, dispersive electrode E and contact M.

When the positive output of this low-frequency oscillator is conducted to dispersive electrode E by turning switches $S_1$ and $S_2$ respectively to contact J and N as shown with the broken lines, a current of reverse polarity flows from the negative output of low-frequency waveform generator G to its positive output successively through load Z, active electrode P and contact M.

FIG. 7 shows the exterior view of a therapeutic device according to the invention, wherein the low-frequency waveform generator G and battery are placed in a cylindrical metal body which acts as the dispersive electrode E, while power switch K is attached to one end of the body, and to the other end of the body is attached active electrode P of a moisture-retentive material, such as a sponge, which soaks up a medicament.

FIG. 8 shows the exterior view of another therapeutic device according to the invention, wherein active electrode P and dispersive electrode E, both comprising a plate electrode and a moisture-retentive material such as a sponge, are joined, and a rubber band is attached to dispersive electrode E in such manner that the device is placeable around the head.

FIG. 9 shows an automatically-operable polarity switch circuit, wherein coils $L_1$ and $L_2$ are wound around yoke Y which is provided at the opposite ends of magnet NS. In this arrangement, on energization of coil $L_1$, iron piece F moves from pole N to pole S, and switches $S_1$ and $S_2$ are switched. When coil $L_2$ is energized, iron piece F immediately is attracted from pole S to pole N.

This switch circuit can be advantageously used in a therapeutic device using a battery, because the circuit is switcheable by a flash current and requires no holding current.

Figure 10:
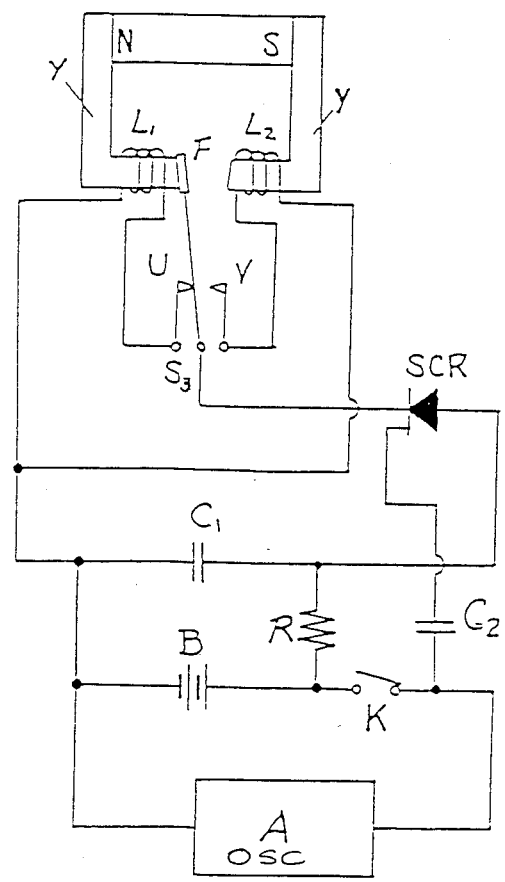
FIGS. 10 and 11 show the circuit for driving the polarity switch.

FIG. 10 illustrates a driving circuit for the polarity switcch, wherein capacitor $C_1$ is charged by battery B through resistor R, and the voltage across the capacitor $C_1$ energizes the anode of thyristor SCR. In this arrangement, when the power switch K is turned on and low-frequency oscillator A is energized, a pulsatile voltage is immediately energized from capacitor $C_2$ to the gate of thyristor SCR to conduct the thyristor. Conduction of thyristor SCR energizes coil $L_1$ to cancel the magnetic force of pole N and, therefore movable iron piece F returns to the center and is immediately attracted to pole S, while switch $S_3$ is turned to contact V. The next conduction of thyristor SCR energizes in turn coil $L_2$ to cancel the magnetic force of pole S, and movable iron piece F is attracted, inversely, to pole N.

In this way, the polarity of the voltage between active electrode P and dispersive electrode E is switched whenever the off/on operation of power switch K reverses the connection of switch $S_3$.

Figure 11:
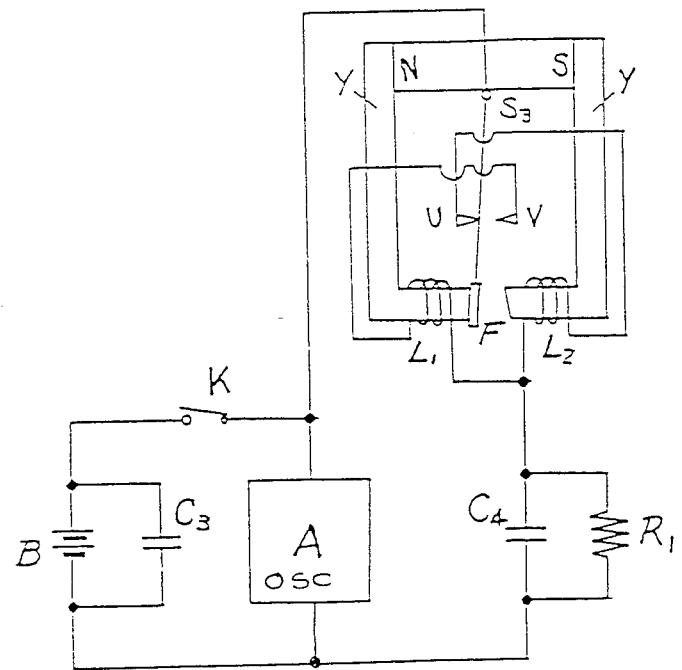

FIG. 11 illustrates another driving circuit for the polarity switch. In the circuit wherein power switch K is closed, a current is supplied to low-frequency oscillator A and, through contact U, to coil $L_2$ to cancel the magnetic force of pole S. Thus, movable iron piece F is attracted to pole N.

In this driving circuit, capacitor $C_3$ connected in parallel with battery B is used to decrease the internal resistance of battery B and is as well used to supply a high flash current. Capacitor $C_4$ is charged through switches K and $S_3$, and either coil $L_1$ or $L_2$, and the charge current energizes either coil $L_1$ or $L_2$ to quickly cancel the magnetic force of pole N or S to return iron piece F to the center.

Resistor $R_1$ connected in parallel with capacitor $C_4$ is used to discharge capacitor $C_4$. When capacitor $C_4$ and resistor $R_1$ are, for example, 100 microfarads and 100 kiloohms respectively, the time constant is 1,000 seconds. Thus, capacitor $C_4$ is discharged for up to 1,000 seconds. By adequately setting the time constant, the driving circuit is not operated when off/on operation of power switch K is carried out during the relatively short time interval, thus the output polarity of oscillator A can be reversed by one- or two-time switchings per day.

As described above, since in the invention the whole of an ionized medicament can be efficiently iontophoresed into the deeper part of the affected site by energizing the output of a low-frequency oscillator to a pair of active- and dispersive-electrodes while switchin the polarity of the output at prescribed time intervals, a higher efficacy which is hardly attainable by iontophoresing either cation or anion is possible by using the therapeutic device of the invention.

Furthermore, since according to the invention the output polarity of a low-frequency oscillator is automatically switched, the whole of an ionized medicament can be easily iontophoresed without switching the output polarity with a complicated switching operation.

While I have shown and described particular embodiments of my invention, it will be obvious to those skilled in the art that various changes and modifications may be made without departing from my invention in its broader aspects and I, therefore, intend in the appended claims to cover all such changes and modifications as fall within the true spirit and scope of my invention.

I claim:

1. A therapeutic device for iontophoresing both cations and anions, comprising:
    a power source including a power switch, said power source being for electrifying the device;
    a first electrode containing an ionized medicament for acting as an active electrode when in use;
    a second electrode for acting as a dispersive electrode when in use;
    means for oscillating a low-frequency current in which an ac current is superposed on a dc current, said oscillating means having output terminals connected with said first and second electrodes for supplying said low-frequency current via said first and second electrodes and medicament to the head of a user; and
    means for switching the output polarity of said oscillating means in association with OFF/ON operation of said power switch, said switching means being provided between said oscillating means and said first and second electrodes, said switching means comprising:
    a magnet,
    a pair of yokes provided at opposite ends of said magnet,
    a pair of coil members provided around the ends of the yokes,
    a piece of magnetic body movably provided between the yokes,
    means for alternately electrifying the coil members in association with the OFF/ON operation of the power switch, and
    a set of electrical contacts openable and closeable in association with the movement of the piece of magnetic body, said electrical contacts being connected with said first and second electrodes in such manner that the polarity of said first and second electrodes is alternately reversed whenever the OFF/ON operation of the power switch is effected.

2. The device of claim 1, wherein said medicament is a member selected from the group consisting of aminovinyl photosensitizing dye and kojic acid.

3. The device of claim 1, wherein said piece of magnetic body is of iron.

* * * * *